United States Patent [19]

Riess et al.

[11] Patent Number: 5,190,947

[45] Date of Patent: Mar. 2, 1993

[54] CODEINE SALT OF A SUBSTITUTED CARBOXYLIC ACID, ITS USE AND PHARMACEUTICAL COMPOSITIONS THEREOF

[75] Inventors: Walter Riess, Basel; Alfred Sallmann, Bottmingen, both of Switzerland

[73] Assignee: Ciba-Geigy Corporation, Ardsley, N.Y.

[21] Appl. No.: 746,676

[22] Filed: Aug. 16, 1991

[30] Foreign Application Priority Data

Aug. 23, 1990 [CH] Switzerland .................. 2735/90

[51] Int. Cl.⁵ .................. A61K 31/485; C07D 489/04
[52] U.S. Cl. .......................... 514/282; 546/44
[58] Field of Search ............ 546/44; 514/282

[56] References Cited

U.S. PATENT DOCUMENTS

| | | | |
|---|---|---|---|
| 936,254 | 7/1910 | Schaeffer | 546/44 |
| 2,628,185 | 2/1953 | Lewenstein | 546/44 X |
| 3,895,063 | 7/1975 | Sallman et al. | 564/433 |
| 4,329,440 | 5/1982 | Kokubo et al. | 526/142 |
| 4,690,927 | 9/1987 | Voss et al. | 514/282 |

FOREIGN PATENT DOCUMENTS

| | | | |
|---|---|---|---|
| 0537946 | 3/1957 | Canada | 546/44 |
| 0377588 | 8/1922 | Fed. Rep. of Germany | 546/44 |
| 2015451 | 11/1970 | Fed. Rep. of Germany | 546/44 |
| 2935776 | 4/1981 | Fed. Rep. of Germany . | |
| 1479209 | 5/1967 | France | 546/44 |
| 37-2646 | 5/1962 | Japan | 546/44 |
| 2170709 | 8/1986 | United Kingdom . | |

*Primary Examiner*—Diana G. Rivers
*Attorney, Agent, or Firm*—Irving M. Fishman; Karen G. Kaiser

[57] ABSTRACT

The invention relates to the codeine salt of [2-[(2,6-dichlorophenyl)-amino]-phenyl]-acetic acid of formula

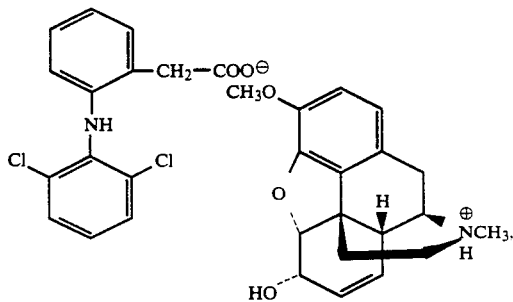

(I)

to processes for the preparation thereof, to pharmaceutical compositions comprising that salt, and to its use as an analgesic drug.

Compositions comprising the salt of formula I are used especially in the case of severe painful conditions.

3 Claims, No Drawings

CODEINE SALT OF A SUBSTITUTED CARBOXYLIC ACID, ITS USE AND PHARMACEUTICAL COMPOSITIONS THEREOF

The present invention relates to a novel codeine salt of a substituted carboxylic acid, which salt is composed of two different components having central and peripheral activities, respectively, and has an increase in the desired analgesic activity and, at the same time, an improvement in taste.

One of the long-existing primary goals of medicine is the alleviation of pain, especially improvements therein. Such alleviation is generally achieved by the administration of medicaments that are centrally or peripherally analgesically active and that, when administered individually or in combination, bring about an increase in the pain threshold. In most cases it is difficult to meet those requirements using a single chemical component since a strong central analgesic drug generally gives rise to considerable accompanying adverse reactions. Peripheral analgesic drugs have other undesirable reactions.

Such undesirable reactions may be gastrointestinal disorders, dizziness, constipation, nausea and vomiting. Therefore, when analgesic drugs are developed for humans not only is the primary effect (analgesia) important but also new compounds are sought that have minimum adverse reactions while having a maximum analgesic effect. There is accordingly a constant demand for an improvement in action, whether this is achieved by the combination or by other means of two active ingredients having the same medical action; for example this may be achieved by a salt composed of cationic and anionic active ingredients, while retaining a single homogeneous compound having the same physical properties, and thus making it possible to reduce the total amount of the active ingredients to the extent that they exhibit no or only minor adverse effects while having a maximum analgesic action. In general, a potentiation of the therapeutic, that is to say analgesic, action, on the one hand, and, on the other, a reduction in undesirable adverse effects are desired.

DE-A-3 603 564 discloses a pharmaceutical composition having a strong analgesic action that is composed of a salt of diclofenac, especially the sodium salt, and a salt of codeine, especially codeine phosphate. It was found that such a desired potentiating action occurs in the case of a combination of a pharmaceutically acceptable salt of diclofenac and a pharmaceutically acceptable salt of codeine. However, the oral administration of the solid combination comprising a 1:1 mixture of diclofenac sodium and codeine phosphate has the disadvantage that it leaves an extremely bitter, lasting taste which is even bitterly sharp in the area of the palate and pharynx and also often irritates to the extent of causing coughing. In particular, this irritant effect and the associated coughing is especially disadvantageous for cancer patients who are administered this mixture comprising diclofenac sodium and codeine phosphate as a strong analgesic drug to combat the pain.

The invention relates to a novel codeine salt of [2-[(2,6-dichlorophenyl)-amino]-phenyl]-acetic acid (diclofenac) of formula

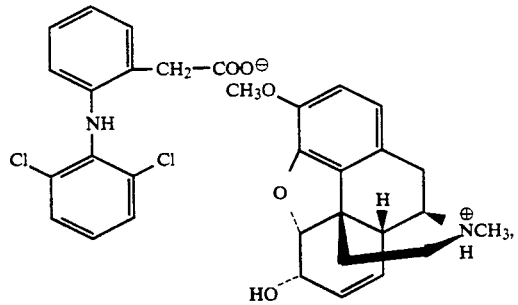

to processes for the preparation thereof, to its use as a medicament, and to pharmaceutical compositions comprising that salt.

It has surprisingly been found that the codeine salt of formula I according to the invention, having a strong analgesic action, is, when in the form of a homogeneous uniform compound, free of the bitter accompanying taste and the irritant effect (coughing) resulting therefrom. Taste comparisons carried out on 4 test persons, where 2 mg of test compound were placed on the tongue and were swallowed only after 30 seconds, showed that the codeine salt of diclofenac of formula I caused no bitter taste on the tongues of 2 of the test persons and caused only a slightly bitter taste on the tongues of the other 2 test persons, whereas the 1:1 mixture of diclofenac sodium and codeine phosphate gave rise in all 4 test persons to a very bitter and caustic taste even on the palate, accompanied by an irritant effect (coughing).

Also worthy of note is a comparison of the $ED_{50}$ values ascertained by the benzoquinone writhing test (combined automated writhing/motility test for testing analgesics, according to A. Schweizer, R. Brom and H. Scherrer, Agents and Actions, Vol. 23, 1/2, 29-31, 1988) which give a value of 4 mg/kg p.o. for the novel codeine salt of formula I in comparison with a value of 6 mg/kg p.o. for the 1:1 mixture of diclofenac sodium and codeine phosphate, and thus the different values speak in favour of the diclofenac-codeine salt as a uniform compound.

The [2-[(2,6-dichlorophenyl)-amino]-phenyl]-acetic acid on which the codeine salt of formula I is based and the salts thereof are known from DE-A-1 815 802 and its ammonium salts, especially, are known from DE-A-2 935 776 and FR-A-2 500 751, as well are its anti-inflammatory and analgesic effects.

The sodium salt (diclofenac sodium) is used, for example, as a non-steroidal antiinflammatory drug in the treatment of inflammatory processes. The corresponding compositions are administered predominantly orally, but also enterally or parenterally.

The second component of the salt of formula I, codeine, is a known centrally active analgesic drug of the opiate type. With regard to the dependence potential of codeine, it can be gathered from the literature that the risk of inducing dependence with the customary oral codeine doses as constituent of the codeine salt of formula I is, under medical supervision, to be regarded as slight.

The invention relates also to processes for the preparation of the novel compound of formula I which are carried out in accordance with methods known per se.

A preferred process variant comprises, for example, reacting [2-[(2,6-dichlorophenyl)-amino]-phenyl]-acetic acid of formula II

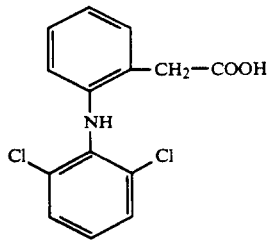
(II)

or a base salt thereof other than the salt of formula I with preferably at least an equimolar amount of codeine of formula III

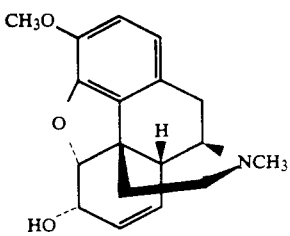
(III)

or salt thereof.

Salts of the acid of formula II that can be used in accordance with the process are especially salts with bases of the kind that can be readily removed from the reaction mixture, for example are more volatile or weaker than the codeine of formula III or form more readily soluble salts with [2-[(2,6-dichlorophenyl)-amino]-phenyl]-acetic acid than does the codeine of formula III, for example organic ammonium salts, and also metal salts that form sparingly soluble salts, such as calcium salts, during the reaction with a suitable salt of the codeine of formula III.

Salts of the codeine of formula III that can be used in accordance with the process are, for example, salts of the same with acids of the kind that can be readily removed from the reaction mixture, for example corresponding codeine salts of volatile acids or of acids that are more weakly acidic than is the corresponding salt of formula I, such as salts of codeine of formula III with inorganic acids, for example phosphates, or salts with organic acids, for example fumarates, maleates or oxalates.

The reaction of [2-[(2,6-dichlorophenyl)-amino]-phenyl]-acetic acid with codeine is advantageously effected in an inert solvent or diluent, if necessary with cooling and heating, for example in a temperature range of from approximately 0° to approximately 100° C., preferably at room temperature, in a closed vessel and-/or under an inert gas atmosphere, for example nitrogen.

Suitable solvents and diluents are, for example, alcohols, such as lower alkanols, for example methanol or ethanol, but especially ethers, such as di-lower alkyl ethers, for example diethyl ether, and cyclic ethers, for example dioxane or tetrahydrofuran, ketones, such as di-lower alkyl ketones, for example acetone, carboxylic acid esters, such as lower alkanecarboxylic acid esters, for example ethyl acetate, amides, such as N,N-di-lower alkylamides, for example N,N-dimethylformamide, sulfoxides, such as di-lower alkyl sulfoxides, for example dimethyl sulfoxide, or mixtures thereof.

[2-[(2,6-dichlorophenyl)-amino]-phenyl]-acetic acid can be formed, for example, under the reaction conditions from corresponding esters, such as lower alkyl esters, by hydrolysis in the presence of a base. Codeine can be used, for example, in the form of an acid addition salt, for example a phosphate, and freed optionally in the presence of a base.

In a preferred form of the process, for example the acid of formula II is reacted in an organic solvent, such as an ether, such as a di-lower alkyl ether, for example diethyl ether, directly with the codeine of formula III in the form of a base. The invention relates also to those forms of the process according to which the starting materials are prepared in situ or in which a starting material is obtained under the reaction conditions from a derivative and/or is used in the form of an isomeric mixture or in the form of a pure isomer.

The invention relates also to pharmaceutical compositions that comprise the salt of formula I and to a process for the preparation of pharmaceutical compositions. The process comprises mixing the compound of formula I with customary excipients and/or adjuvants.

In this connection, the invention relates especially to the pharmaceutical compositions described in the Examples and to processes for the preparation thereof.

The pharmaceutical compositions according to the invention, which comprise compounds of formula I, are compositions for enteral, such as oral or rectal, and parenteral administration and also for topical administration to (a) warm-blooded animal(s) that comprise the pharmacological acitve ingredient alone or together with a pharmaceutically acceptable carrier. The dose of the active ingredient depends on the species of warm-blooded animal, age and individual condition, and also on the method of administration.

Suitable unit dose forms for oral administration are, for example, tablets, enteric-coated tablets (tablets having enteric coatings), dragées and capsules that comprise from 50 to 300 mg, preferably from 100 to 250 mg, of diclofenac-codeine salt. Suppositories and capsules for rectal administration comprise from 50 to 200 mg, preferably from 50 to 150 mg, of diclofenac-codeine salt. The unit dose forms are administered from once to three times daily in a number that corresponds to a daily dose of from 150 to 300 mg of diclofenac-codeine for adult patients or to doses reduced in accordance with age and body weight for children.

In unit dose forms for peroral administration, the combined content of the two compounds used as active ingredients is preferably from 20% to 90%. In order to prepare tablets or dragée cores, the active ingredients are combined, for example, with solid, pulverulent carriers, such as lactose, sucrose, sorbitol, mannitol; starches, such as potato starch, cornstarch or amylopectin, and also laminaria powder or citrus pulp powder, cellulose derivatives, gelatin or polyvinylpyrrolidone, where appropriate with the addition of glidants, such as magnesium or calcium stearate or polyethylene glycols, or highly dispersed silicic acid. Dragée cores are then coated, for example, with concentrated sugar solutions, which may also contain, for example, gum arabic, talc and/or titanium dioxide, or with a lacquer dissolved in readily volatile organic solvents or solvent mixtures. It is possible to add colourings to those coatings, for example to indicate different doses of active ingredient. Suitable oral unit dose forms are also dry-filled capsules consisting of gelatin, and also soft, sealed capsules consisting of gelatin and a plasticiser, such as glycerol. The former contain the active ingredients preferably in the form of granules in admixture with glidants, such as talc or magnesium stearate, and optionally stabilisers, such as sodium metabisulfite ($Na_2S_2O_5$) or ascorbic acid. In soft capsules, the active ingredients are preferably dissolved or suspended in suitable liquids, such as liquid polyethylene glycols, to which stabilisers may also be added.

Suitable unit dose forms for rectal administration are, for example, suppositories that comprise the active ingredient salt (itself a combination of active ingredients) with a suppository base based on natural or synthetic triglycerides having a suitable melting point (for example cocoa butter), polyethylene glycols or suitable higher fatty alcohols, and gelatin rectal capsules that comprise a combination of the active ingredient and polyethylene glycols.

Suitable for parenteral administration are especially solutions of the active ingredient, and also suspensions thereof, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain viscosity-increasing substances, for example sodium carboxymethylcellulose, sorbitol and/or dextran and, where appropriate, also stabilisers.

Suitable topically administrable pharmaceutical compositions are especially creams, ointments, pastes, foams, tinctures and solutions that comprise from approximately 0.5 to approximately 20% active ingredient.

Creams are oil-in-water emulsions comprising more than 50% water. There are used as oily base especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. Suitable as emulsifiers are surface-active substances having predominantly hydrophilic properties, such as corresponding non-ionic emulsifiers, for example fatty acid esters of polyalcohols or ethylene oxide adducts thereof, such as polyglycerol fatty acid esters or polyoxyethylene fatty alcohol ethers or polyoxyethylene fatty acid esters, or corresponding ionic emulsifiers, such as alkali metal salts of fatty alcohol sulfates, for example sodium lauryl sulfate, sodium cetyl sulfate or sodium stearyl sulfate, which are normally used in the presence of fatty alcohols, for example cetyl alcohol or stearyl alcohol. Adjuvants to the aqueous phase are, inter alia, agents that reduce the drying-out of the creams, for example polyalcohols, such as glycerol, sorbitol, propylene glycol and/or polyethylene glycols, and also preservatives, perfumes, etc.

Ointments are water-in-oil emulsions comprising up to 70%, but preferably from approximately 20% to approximately 50%, water or aqueous phases. Suitable as the fatty phase are especially hydrocarbons, for example petroleum jelly, paraffin oil and/or hard paraffins, which, in order to improve the water-binding capacity, preferably comprise suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerol, propylene glycol, sorbitol and/or polyethylene glycol, and also preservatives, perfumes, etc.

Fatty ointments are anhydrous and comprise as base especially hydrocarbons, for example paraffin, petroleum jelly and/or liquid paraffins, and also natural or partially synthetic fats, for example coconut fatty acid triglyceride, or preferably hardened oils, for example hydrogenated groundnut or castor oil, also fatty acid partial esters of glycerol, for example glycerol mono- or di-stearate, and also, for example, the fatty alcohols increasing the water-absorption capacity, emulsifiers and/or adjuvants mentioned in connection with the ointments.

Pastes are creams and ointments having secretion-absorbing powder constituents, such as metal oxides, for example titanium oxide or zinc oxide, and also talc and/or aluminium silicates the purpose of which is to bind any moisture or secretions present.

Foams are administered from pressurised containers and are liquid oil-in-water emulsions in aerosol form; halogenated hydrocarbons, such as chlorofluoro-lower alkanes, for example dichlorodifluoromethane and dichlorotetrafluoroethane, are used as propellants. There are used as the oily phase, inter alia, hydrocarbons, for example paraffin oil, fatty alcohols, for example cetyl alcohol, fatty acid esters, for example isopropyl myristate, and/or other waxes. There are used as emulsifiers, inter alia, mixtures of emulsifiers having predominantly hydrophilic properties, such as polyoxyethylenesorbitan fatty acid esters (Tweens), and emulsifiers having predominantly lipophilic properties, such as sorbitan fatty acid esters (Spans). The customary adjuvants, such as preservatives, etc., are also added.

Tinctures and solutions generally have an aqueous-ethanolic base to which are added, inter alia, polyalcohols, for example glycerol, glycols and/or polyethylene glycol, as humectants for reducing evaporation, and fat-restoring substances, such as fatty acid esters with low-molecular-weight polyethylene glycols, that is to say, lipophilic substances that are soluble in the aqueous mixture, as a replacement for the fatty substances removed from the skin by the ethanol, and, if necessary, other excipients and adjuvants.

The preparation of the topically administrable pharmaceutical compositions is carried out in a manner known per se, for example by dissolving or suspending the active ingredient in the base or, if necessary, in a part thereof. When processing the active ingredient in the form of a solution, it is generally dissolved in one of the two phases before emulsification; when processing the active ingredient in the form of a suspension, it is added after emulsification. The concentration of active ingredient is approximately from 0.5 to 10% by weight, for example from 0.5 to 5% by weight.

The following Examples illustrate the invention described above but are not intended to limit its scope in any way. Temperatures are given in degrees Celsius and pressures in mbar.

EXAMPLE 1 a) 17.84 g of codeine are dissolved in a round-bottomed flask placed on a water bath, the flask containing 1300 ml of ether. A solution of 17.65 g of [2-[(2,6-dichlorophenyl)-amino]-phenyl]-acetic acid in 500 ml of ether is added to the first solution and part of the ether solvent is removed by distillation, a hard crystal crust being formed on the wall of the flask. After concentrating the total volume of ether to approximately 100 ml and cooling the reaction mixture to 5° C., the contents of the flask are filtered with suction and the resulting material retained on the filter is washed several times with ether and then sieved (sieve 180μ) after being dried at 40° C. under a high vacuum.

Colourless crystals of the codeine salt of [2-[(2,6-dichlorophenyl)-amino]-phenyl]-acetic acid having a melting point of from 162° to 165° C. are obtained.

b) The free codeine base is obtained as follows: 25.00 g of codeine phosphate are dissolved in 100 ml of ice-water (mixture of ice and water) and the resulting solution mixture is rendered alkaline with concentrated sodium hydroxide solution. The resinous precipitate is taken up in ether, and again (twice) concentrated sodium hydroxide solution and water are added until two clear phases are obtained. The aqueous phase is extracted several times (3×) with ether and all the collected organic phases are dried over magnesium sulfate and then concentrated in vacuo. Petroleum ether is added to the resulting residue and the batch is filtered with suction to give the free codeine base which has a melting point of from 155° to 156° C.

EXAMPLE 2

3.18 g of the sodium salt of [2-[(2,6-dichlorophenyl)-amino]-phenyl]-acetic acid are dissolved at 65° C. with stirring in 100 ml of water. The solution is cooled rapidly to 40° C., with stirring, using an ice bath, and a solution of 4.0 g of codeine phosphate in 50 ml of water is added immediately. The resulting suspension is cooled to 0° C. with stirring and filtered. The material retained on the filter is triturated with 10 ml of hot water and the suspension is stirred for 10 minutes and then filtered. The resulting material on the filter is recrystallised twice from ethanol.

The codeine salt of [2-[(2,6-dichlorophenyl]-amino]-phenyl]-acetic acid melts at from 162° to 165° C.

EXAMPLE 3

3.69 g of the diethyl ammonium salt of [2-[(2,6-dichlorophenyl)-amino]-phenyl]-acetic acid are dissolved at 65° C. with stirring in 70 ml of water. The solution is cooled to 40° C. and a solution of 3.97 g of codeine phosphate in 30 ml of water is added. The crystals which separate out are isolated by filtration and triturated with 10 ml of hot water. The suspension is filtered again and the resulting solid residue is recrystallised from ethanol.

The codeine salt of [2-[(2,6-dichlorophenyl)-amino]-phenyl]-acetic acid melts at from 162° to 165° C.

EXAMPLE 4

Preparation of Film-Coated Tablets 400 g of diclofenac codeine salt are mixed thoroughly with 480 g of dicalcium phosphate, 280 g of cornstarch and 48 g of colloidal silica. The mixture is spray-granulated with a solution of 64 g of hydroxypropylcellulose (Klucel L) in 1216 g of deionised water in an apparatus suitable for the purpose and dried. The dried granules are passed through a 1-mm sieve. 225 g of sodium carboxymethyl starch (Primojel), 20 g of colloidal silica and 8 g of magnesium stearate are then admixed with the sieved granules. The finished mixture is compressed in known manner to form tablets weighing 340 mg. The tablets are oblong in shape and have a breaking notch. The tablet cores are then provided with a coating which serves to make the tablet easy to swallow. To that end, 10 mg of coating substance (non-enteric) per tablet are applied in known manner in a suitable apparatus. For that purpose, hydroxypropylmethylcellulose (Pharmacoat), polyoxyethylene sorbitan fatty acid ester (Tween), titanium dioxide and talcum are dissolved or suspended in deionised water.

The coated tablet disintegrates rapidly in water or physiological media and releases the active ingredients.

1 film-coated tablet weighing 350 mg comprises: 100 mg of diclofenac-codeine salt.

EXAMPLE 5

Preparation Of Suppositories

Extremely finely ground diclofenac-codeine salt is suspended in a melted suppository base (hard fat, Ph. Eur. Volume III, having a hydroxy number of <5). Fat-soluble colourings (for example chlorophyll) or colouring pigments may be added. The suspension is cast in moulds in known manner. Either the moulds are prefabricated from plastics and serve after bonding as packaging or the moulds are made of metal. The suppositories are released therefrom after cooling and bonded into foil sheets. The suppositories are normally torpedo-shaped, white or coloured and weight approximately 2 g. After rectal administration, the suppositories melt and release the incorporated active ingredients.

1 suppository comprises: 100 mg of diclofenac-codeine salt.

What is claimed is:

1. The codeine salt of [2-[(2,6-dichlorophenyl)-amino]-phenyl]-acetic acid of formula

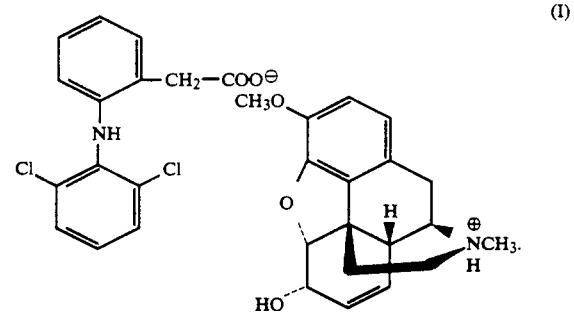

(I)

2. A pharmaceutical composition comprising an analgesically effective amount of the codeine salt of [2-[(2,6-dichlorophenyl)-amino]-phenyl]-acetic acid of claim 1 together with a customary pharmaceutical excipient.

3. A method of treating pain, which comprises administering to a warm-blooded organism requiring such treatment a pharmaceutical composition according to claim 2.

* * * * *